(12) United States Patent
Barratt et al.

(10) Patent No.: US 6,383,782 B1
(45) Date of Patent: May 7, 2002

(54) MCP-1 ANALOGS

(75) Inventors: Derek Graham Barratt; Maurice Ronald Charles Needham, both of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/463,458

(22) PCT Filed: Jul. 21, 1998

(86) PCT No.: PCT/GB98/02179

§ 371 Date: Jan. 27, 2000

§ 102(e) Date: Jan. 27, 2000

(87) PCT Pub. No.: WO99/05279

PCT Pub. Date: Feb. 4, 1999

(30) Foreign Application Priority Data

Jul. 25, 1997 (GB) .............................................. 9715659
Jul. 25, 1997 (GB) .............................................. 9715661
Jul. 25, 1997 (GB) .............................................. 9715663

(51) Int. Cl.$^7$ ........................ C12N 21/00; C12N 21/02; C12N 15/70; C12N 15/64; A61K 38/19
(52) U.S. Cl. .................. 435/69.5; 435/69.1; 435/320.1; 435/325; 514/2; 530/300; 424/85.1
(58) Field of Search ........................ 530/300; 435/69.5, 435/320.1, 69.1, 325, 252.3, 419, 254.11; 514/2; 424/85.1

(56) References Cited

U.S. PATENT DOCUMENTS 5,013,662 A    5/1991   Ben-Bassat et al.
5,573,930 A    11/1996  Ladner et al.

FOREIGN PATENT DOCUMENTS

CA    2152141    12/1996
WO    92/19737   11/1992

OTHER PUBLICATIONS

Miller et al., N–Terminal methionine–Specific Peptidase in *Salmonella Typhimurium*, Proc. Natl. Acad. Sci. USA, May 1987, pp. 2718–2722.

Zhang et al., Structure/activity analysis of human monocyte chemoattractant protein–1 (MPC–1) by mutagenesis, Journal of Biological Chemistry, Jun. 3, 1994, pp. 15918–15924, vol. 269, No. 22, USA.

*Primary Examiner*—Elizabeth Kemmerer
*Assistant Examiner*—Regina M. DeBerry
(74) *Attorney, Agent, or Firm*—Rothwell, Figg, Ernst & Manbeck

(57) ABSTRACT

Novel Analogues of Monocyte Chemoattractant Protein-1 (MCP-1) have substitution of an alanine, glycine or threonine for the natural valine in position 9 of MCP-1 (9-76).

14 Claims, 8 Drawing Sheets

SEQUENCE LISTING

<160> NUMBER OF SEQ ID NOS: 32

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 1
gcgcatatgg ctacttgttg ttataacttt accaaccgta aaatttctgt tcagcgcctg      60

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: 3' PCR
      primer

<400> SEQUENCE: 2
gggatcctca tcaggtcttc ggggtctggg tctgt                                 35

<210> SEQ ID NO 3
<211> LENGTH: 117
<212> TYPE: DNA
<213> ORGANISM: Artificial Sequence
<220> FEATURE:
<223> OTHER INFORMATION: Description of Artificial Sequence:
      oligonucleotide sequence of MCP-1

<400> SEQUENCE: 3
gttacttgtt gttataactt taccaaccgt aaaatttctg ttcagcgcct ggcatcctac      60
cgtcgtatca cctcctctaa atgtccgaaa gaagctgtta tcttcaagac catcgtt       117

<210> SEQ ID NO 4
<211> LENGTH: 121
<212> TYPE: DNA
<213> ORGANISM: Artificial Sequence

```
<220> FEATURE:
<223> OTHER INFORMATION: Description of Artificial Sequence:
      oligonucleotide sequence of MCP-1

<400> SEQUENCE: 4
tcaggtcttc ggggtctggg tctgtttgtc caggtggtcc atggagtcct gaacccactt    60
ctgtttcggg tcagcacaga tttctttagc aacgatggtc ttgaagataa cagcttcttt   120
c                                                                    121

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 5
gcgcatatgg ttacttgttg ttataacttt accaaccgta aaatttctgt tcagcgcctg    60

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 6
gcgccatggc ggtcacctgc tgttataact tc                                  32

<210> SEQ ID NO 7
<211> LENGTH: 72
<212> TYPE: DNA
<213> ORGANISM: Artificial Sequence
<220> FEATURE:
<223> OTHER INFORMATION: Description of Artificial Sequence: 3' PCR
      primer

<400> SEQUENCE: 7
gcgctcgagt caagtcttcg gagtttgggt ttgcttgtcc aggtggtcca ttgaatcctg    60
aacccacttc tg                                                        72

<210> SEQ ID NO 8
<211> LENGTH: 207
<212> TYPE: DNA
<213> ORGANISM: Artificial Sequence
<220> FEATURE:
<223> OTHER INFORMATION: Description of Artificial Sequence:
      polynucleotide sequence for [V9A]MCP-1(9-76)

<400> SEQUENCE: 8
gctacttgtt gttataactt taccaaccgt aaaatttctg ttcagcgcct ggcatcctac    60
cgtcgtatca cctcctctaa atgtccgaaa gaagctgtta tcttcaagac catcgttgct   120
aaagaaatct gtgctgaccc gaaacagaag tgggttcagg actccatgga ccacctggac   180
aaacagaccc agaccccgaa gacctga                                       207

<210> SEQ ID NO 9
<211> LENGTH: 68
<212> TYPE: PRT
<213> ORGANISM: Artificial Sequence
<220> FEATURE:
<223> OTHER INFORMATION: Description of Artificial Sequence:
```

[V9A]MCP-1(9-76)

<400> SEQUENCE: 9

Ala Thr Cys Cys Tyr Asn Phe Thr Asn Arg Lys Ile Ser Val Gln Arg
 1               5                  10                  15

Leu Ala Ser Tyr Arg Arg Ile Thr Ser Ser Lys Cys Pro Lys Glu Ala
             20                  25                  30

Val Ile Phe Lys Thr Ile Val Ala Lys Glu Ile Cys Ala Asp Pro Lys
         35                  40                  45

Gln Lys Trp Val Gln Asp Ser Met Asp His Leu Asp Lys Gln Thr Gln
     50                  55                  60

Thr Pro Lys Thr
 65

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: 5' PCR
      primer #1

<400> SEQUENCE: 10
gatgctataa tgcatgacac catcgaatgg cgcaa                         35

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: 3' PCR
      primer #2

<400> SEQUENCE: 11
cagtatgcac agtatgcatt tacattaatt gcgttgcgct c                  41

<210> SEQ ID NO 12
<211> LENGTH: 88
<212> TYPE: DNA
<213> ORGANISM: Artificial Sequence
<220> FEATURE:
<223> OTHER INFORMATION: Description of Artificial Sequence: 5'-3'
      oligomer #3

<400> SEQUENCE: 12
aattccagac atatggtacc agtactctat actagttgaa ggatccatgc ctcgagaacg   60
ctgcagagct aagcttgaca agatctaa                                     88

<210> SEQ ID NO 13
<211> LENGTH: 88
<212> TYPE: DNA
<213> ORGANISM: Artificial Sequence
<220> FEATURE:
<223> OTHER INFORMATION: Description of Artificial Sequence: 3'-5'
      oligomer #4

<400> SEQUENCE: 13
gatcttagat cttgtcaagc ttagctctgc agcgttctcg aggcatggat ccttcaacta   60
gtatagagta ctggtaccat atgtctgg                                     88

<210> SEQ ID NO 14
<211> LENGTH: 105
<212> TYPE: DNA

```
<213> ORGANISM: Artificial Sequence
<220> FEATURE:
<223> OTHER INFORMATION: Description of Artificial Sequence: 5'-3'
      oligomer #5

<400> SEQUENCE: 14
agcttaacaa agcccgaaag gaagctgagt tggctgctgc caccgctgag caataactag    60
cataacccct tggggcctct aaacgggtct tgagggtttt tttga                  105

<210> SEQ ID NO 15
<211> LENGTH: 105
<212> TYPE: DNA
<213> ORGANISM: Artificial Sequence
<220> FEATURE:
<223> OTHER INFORMATION: Description of Artificial Sequence: 3'-5'
      oligomer #6

<400> SEQUENCE: 15
gatctcaaaa aacccctcaa gacccgttta gaggccccaa ggggttatgc tagttattgc    60
tcagcggtgg cagcagccaa ctcagcttcc tttcgggctt tgtta                  105

<210> SEQ ID NO 16
<211> LENGTH: 90
<212> TYPE: DNA
<213> ORGANISM: Artificial Sequence
<220> FEATURE:
<223> OTHER INFORMATION: Description of Artificial Sequence: 5'-3'
      oligomer #7

<400> SEQUENCE: 16
tcgaggcatt gtcctcttag ttaaatggat ataacgagcc cctcctaagg gctaattgca    60
ggttcgattc ctgcagggga ctccactgca                                    90

<210> SEQ ID NO 17
<211> LENGTH: 82
<212> TYPE: DNA
<213> ORGANISM: Artificial Sequence
<220> FEATURE:
<223> OTHER INFORMATION: Description of Artificial Sequence: 3'-5'
      oligomer #8

<400> SEQUENCE: 17
gtggagtccc ctgcaggaat cgaacctgca attagccctt aggaggggct cgttatatcc    60
atttaactaa gaggacaatg cc                                            82

<210> SEQ ID NO 18
<211> LENGTH: 71
<212> TYPE: DNA
<213> ORGANISM: Artificial Sequence
<220> FEATURE:
<223> OTHER INFORMATION: Description of Artificial Sequence: 5'-3'
      oligomer #9

<400> SEQUENCE: 18
cctattatat tactaattaa ttggggaccc tagaggtccc ctttttttatt ttaaaaccat    60 ggaaccaacc g                                                        71

<210> SEQ ID NO 19
<211> LENGTH: 75
<212> TYPE: DNA
<213> ORGANISM: Artificial Sequence
<220> FEATURE:
<223> OTHER INFORMATION: Description of Artificial Sequence: 3'-5'
      oligomer #10
```

<400> SEQUENCE: 19
aattcggttg gttccatggt tttaaaataa aaaagggggac ctctagggtc cccaattaat    60
tagtaatata atagg    75

<210> SEQ ID NO 20
<211> LENGTH: 97
<212> TYPE: DNA
<213> ORGANISM: Artificial Sequence
<220> FEATURE:
<223> OTHER INFORMATION: Description of Artificial Sequence: 5'-3'
      oligomer #11

<400> SEQUENCE: 20
aattccgaaa ttaatacgac tcactatagg ggaattgtga gcgctcacaa ttcccctcta    60
gaaataattt tgtttaactt taagaaggag atataca    97

<210> SEQ ID NO 21
<211> LENGTH: 95
<212> TYPE: DNA
<213> ORGANISM: Artificial Sequence
<220> FEATURE:
<223> OTHER INFORMATION: Description of Artificial Sequence: 3'-5'
      oligomer #12

<400> SEQUENCE: 21
tatgtatatc tccttcttaa agttaaacaa aattatttct agaggggaat tgtgagcgct    60
cacaattccc ctatagtgag tcgtattaat ttcgg    95

<210> SEQ ID NO 22
<211> LENGTH: 85
<212> TYPE: DNA
<213> ORGANISM: Artificial Sequence
<220> FEATURE:
<223> OTHER INFORMATION: Description of Artificial Sequence: 5'-3'
      oligomer #13

<400> SEQUENCE: 22
catggacgtg ttaacaacca accggaattg tgagcgctca caattccatc caagaacaac    60
catcctagca acacggcggt ccccg    85

<210> SEQ ID NO 23
<211> LENGTH: 85
<212> TYPE: DNA
<213> ORGANISM: Artificial Sequence
<220> FEATURE:
<223> OTHER INFORMATION: Description of Artificial Sequence: 3'-5'
      oligomer #14

<400> SEQUENCE: 23
aattcgggga ccgccgtgtt gctaggatgg ttgttcttgg atggaattgt gagcgctcac    60
aattccggtt ggttgttaac acgtc    85

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 24
gcgcatatgg gtacttgttg ttataac    27

-continued

```
<210> SEQ ID NO 25
<211> LENGTH: 207
<212> TYPE: DNA
<213> ORGANISM: Artificial Sequence
<220> FEATURE:
<223> OTHER INFORMATION: Description of Artificial Sequence:
      polynucleotide sequence for [V9G]MCP-1(9-76)

<400> SEQUENCE: 25
ggtacttgtt gttataactt taccaaccgt aaaatttctg ttcagcgcct ggcatcctac     60
cgtcgtatca cctcctctaa atgtccgaaa gaagctgtta tcttcaagac catcgttgct    120
aaagaaatct gtgctgaccc gaaacagaag tgggttcagg actccatgga ccacctggac    180
aaacagaccc agaccccgaa gacctga                                        207

<210> SEQ ID NO 26
<211> LENGTH: 68
<212> TYPE: PRT
<213> ORGANISM: Artificial Sequence
<220> FEATURE:
<223> OTHER INFORMATION: Description of Artificial Sequence:
      [V9G]MCP-1(9-76)

<400> SEQUENCE: 26

Gly Thr Cys Cys Tyr Asn Phe Thr Asn Arg Lys Ile Ser Val Gln Arg
  1               5                  10                  15

Leu Ala Ser Tyr Arg Arg Ile Thr Ser Ser Lys Cys Pro Lys Glu Ala
             20                  25                  30

Val Ile Phe Lys Thr Ile Val Ala Lys Glu Ile Cys Ala Asp Pro Lys
         35                  40                  45

Gln Lys Trp Val Gln Asp Ser Met Asp His Leu Asp Lys Gln Thr Gln
     50                  55                  60

Thr Pro Lys Thr
 65

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 27
gcgcatatga ccacttgttg ttataac                                         27

<210> SEQ ID NO 28
<211> LENGTH: 207
<212> TYPE: DNA
<213> ORGANISM: Artificial Sequence
<220> FEATURE:
<223> OTHER INFORMATION: Description of Artificial Sequence:
      ploynucleotide sequence for [V9T]MCP-1(9-76)

<400> SEQUENCE: 28
accacttgtt gttataactt taccaaccgt aaaatttctg ttcagcgcct ggcatcctac     60
cgtcgtatca cctcctctaa atgtccgaaa gaagctgtta tcttcaagac catcgttgct    120
aaagaaatct gtgctgaccc gaaacagaag tgggttcagg actccatgga ccacctggac    180
aaacagaccc agaccccgaa gacctga                                        207
```

<210> SEQ ID NO 29
<211> LENGTH: 68
<212> TYPE: PRT
<213> ORGANISM: Artificial Sequence
<220> FEATURE:
<223> OTHER INFORMATION: Description of Artificial Sequence:
[V9T]MCP-1(9-76)

<400> SEQUENCE: 29

Thr Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
    50                  55                  60

Thr Pro Lys Thr
65

<210> SEQ ID NO 30
<211> LENGTH: 68
<212> TYPE: PRT
<213> ORGANISM: Artificial Sequence
<220> FEATURE:
<223> OTHER INFORMATION: Description of Artificial Sequence: MCP1(9-76)

<400> SEQUENCE: 30

Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
    50                  55                  60

Thr Pro Lys Thr
65

<210> SEQ ID NO 31
<211> LENGTH: 69
<212> TYPE: PRT
<213> ORGANISM: Artificial Sequence
<220> FEATURE:
<223> OTHER INFORMATION: Description of Artificial Sequence:
Met-MCP1(9-76)

<400> SEQUENCE: 31

Met Val Thr Cys Cys Tyr Asn Phe Thr Asn Arg Lys Ile Ser Val Gln
1               5                   10                  15

Arg Leu Ala Ser Tyr Arg Arg Ile Thr Ser Ser Lys Cys Pro Lys Glu
            20                  25                  30

Ala Val Ile Phe Lys Thr Ile Val Ala Lys Glu Ile Cys Ala Asp Pro
        35                  40                  45

Lys Gln Lys Trp Val Gln Asp Ser Met Asp His Leu Asp Lys Gln Thr
    50                  55                  60

Gln Thr Pro Lys Thr
65

<210> SEQ ID NO 32
<211> LENGTH: 69

```
<212> TYPE: PRT
<213> ORGANISM: Artificial Sequence
<220> FEATURE:
<223> OTHER INFORMATION: Description of Artificial Sequence:
      pGlu-MCP1(9-76)
<221> NAME/KEY: VARIANT
<222> LOCATION: ()..()
<223> OTHER INFORMATION: Xaa=pGlu

<400> SEQUENCE: 32

Xaa Val Thr Cys Cys Tyr Asn Phe Thr Asn Arg Lys Ile Ser Val Gln
 1               5                  10                  15

Arg Leu Ala Ser Tyr Arg Arg Ile Thr Ser Ser Lys Cys Pro Lys Glu
            20                  25                  30

Ala Val Ile Phe Lys Thr Ile Val Ala Lys Glu Ile Cys Ala Asp Pro
            35                  40                  45

Lys Gln Lys Trp Val Gln Asp Ser Met Asp His Leu Asp Lys Gln Thr
        50                  55                  60

Gln Thr Pro Lys Thr
65
```

MCP-1 ANALOGS

This application is a national stage application of PCT/GB98/02179, filed Jul. 21, 1998.

The present invention relates to novel analogues of Monocyte Chemoattractant Protein-1 (MCP-1) and corresponding potynucleotide sequences vectors. host cells and recombinant expressions particularly in E. coli.

MCP-1 is a member of the chemokine family of proinflammatory cytokines which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis (RA), glomerular nephritides, lung fibrosis, restenosis (International Patent Application WO 94/09128), alveolitis (Jones et al. 1992, J. Immunol. 49, 2147) and asthma. Other disease areas where MCP-1 is thought to play a part in their pathology are: atherosclerosis (e.g. Koch et al. 1992 J. Clin. Invest. 90, 772–779); psoriasis (Deleuran et al. 1996 J. Dermatological Science 13, 228–236), delayed -type hypersensitivity reactions of the skin; inflammatory bowel disease (Grimm et al. 1996 J. Leukocyte Biol. 59, 804–812), multiple sclerosis and; brain trauma (Berman et al. 1996 J. Immunol. 156, 3017–3023). An MCP-1 inhibitor may also be useful to treat stroke, reperfusion injury, ischemia, myocardial infarction and transplant rejection.

It is known that analogues of MCP-1 can be prepared which are antagonistic to its biological properties. Rollins in U.S. Pat. No. 5,459,128 describes MCP-1 antagonists which include truncation at the N-terminus of the protein. Gong in J. Exp. Med. (1995) 181, 631, describes a particular MCP-1 antagonist of this type which is MCP1(9-76) (SEQ ID NO: 30). Gong made MCP-1(9-76) (SEQ ID NO: 30) by direct chemical synthesis. Chemical synthesis is not a commercially attractive process for manufacture of MCP-1(9-76) (SEQ ID NO: 30). Lewis & Gong in Canadian patent application 2152141 describe chemically synthesised MCP-1 analogues which are truncated at the N-tenninus. Conservative amino acid substitutions for some amino acids (excluding valine) are also described therein (see page 7) but preferably only at regions beyond position 35 of MCP-1.

A recombinant method would be preferable for large scale commercial manufacture of MCP1(9-76) (SEQ ID NO: 30) but to date there has been no specific experimental disclosure of any such recombinant methodology.

A preferred organism for recombinant manufacture is E. coli because of its ease of handling. However, Rollins U.S. Pat. No. 5,459,128 warns of problems with use of bacterial expression systems due to incorrect protein folding and states a preference for COS cell expression systems (see column 2, lines 49–51). However, COS cells are not desirable for large scale manufacture because they only provide a transient expression system. We have discovered in our experiments (which are presently unpublished) that secretory expression (i.e. using a leader sequence to direct expressed protein through the cytoplasmic membrane) of MCP1(9-76) (SEQ ID NO: 30) in E. coli has the disadvantage of giving poor yields (see Comparative Example 2). Furthermore we have also discovered that when a polynucleotide encoding MCP1(9-76) is expressed intracellularly in E. coli the resulting product is undesirably heterogeneous due to the presence of an additional methionine residue at the N-terminus in a significant proportion (typically 50%) of the product. There thus exists a need for an improved way of making a MCP1(9-76) (SEQ ID NO: 30) type protein, particularly in E. coli.

The present invention is based on the discovery that substitution of an alanine, glycine or threonine for the natural valine in position 9 of MCP1(9-76) gives a novel MCP-1 analogue (termed "[V9A]MCP1(9-76)" (SEQ ID NO: 9), "[V9G]MCP1(9-76)" (SEQ ID NO: 26) or "[V9T]MCP1(9-76)" (SEQ ID NO: 29) respectively herein) which can be recombinantly manufactured in E. coli to produce a substantially homogeneous product (at least substantially lacking unwanted methionine at the N-terminus) in good yield which retains the antagonistic effect of MCP1(9-76) as measured in the chemotaxis assay described herein.

According to one aspect of the present invention there is provided a protein selected from [V9A]MCP1(9-76) (SEQ ID NO: 9), [V9G]MCP1(9-76) (SEQ ID NO: 26) or [V9T] MCP1(9-76) (SEQ ID NO: 29). The protein sequences of [V9A]MCP1(9-76), [V9G]MCP1(9-76) and [V9T]MCP1 (9-76) are set out in SEQ ID NO: 9, 26 and 29 respectively. Preferably the protein is selected from [V9A]MCP1(9-76) (SEQ ID NO: 9) or [V9G]MCP1(9-76) (SEQ ID NO: 26) and of these [V9A]MCP1(9-76) (SEQ ID NO: 9) is especially preferred.

Note Lewis & Gong in Canadian patent application 2152141 describe conservative amino acid substitutions in truncated MCP-1 analogues but these are preferably beyond position 35 (of MCP-1) and furthermore that disclosure is completely silent on substitution of valine anywhere in the molecule. Preferably the [V9A]MCP1(9-76) (SEQ ID NO: 9), [V9G]MCP1(9-76) (SEQ ID NO: 26) or [V9T]MCP1 (9-76) (SEQ ID NO: 29) is essentially free of methionine at its N-terminus. The term "essentially free" in this context means that methionine is present at a level of about 10% or less (when) analysed by any one of reverse phase HPLC, capillary zone electrophoresis, Edman degradation and electrospray mass spectrometry) at the N-terminus of [V9A] MCP1(9-76) (SEQ ID NO: 9), [V9G]MCP1(9-76) (SEQ ID NO: 26) or [V9T]MCP1(9-76) (SEQ ID NO: 29), preferably methionine is present at a level of less than 5% at the N-terminus of [V9A]MCP1(9-76) (SEQ ID NO: 9), [V9G] MCP1(9-76) or [V9T]MCP1(9-76) (SEQ ID NO: 29), preferably methionine is present at a level of less than 3% at the N-terminus of [V9A]MCP1(9-76) (SEQ ID NO: 9), [V9G] MCP1(9-76) (SEQ ID NO: 26) or [V9-76) (SEQ ID NO: 29), more preferably methionine is present at a level of less than 1% at the N-terminus of [V9A]MCP1(9-76) (SEQ ID NO: 9), [V9G]MCP1(9-76) (SEQ ID NO: 26) or [V9T] MCP1(9-76) (SEQ ID NO: 29), more preferably methionine is present at a level of less than 0.3% at the N-terminus of [V9A]MCP1(9-76) (SEQ ID NO: 9), [9G]MCP1(9-76) (SEQ ID NO: 26) or [V9T]MCP1(9-76) (SEQ ID NO: 29) and more preferably methionine is present at a level of less than 0.1% at the N-terminus of [V9A]MCP1(9-76) (SEQ ID NO: 9), [V9G]MCP1(9-76) (SEQ ID NO: 26) or [V9T] MCP1(9-76) (SEQ ID NO: 29). Preferably the [V9A]MCP1 (9-76) (SEQ ID NO: 9), [V9G]MCP1(9-76) (SEQ ID NO: 26). [V9T]MCP1 (9-76) (SEQ ID NO: 29) gives a single peak when analysed by reverse phase HPLC.

According to another aspect of the invention there is provided a polynucleotide sequence encoding a protein selected from [V9A]MCP1(9-76) (SEQ ID NO: 9), [V9G] MCP1(9-76) (SEQ ID NO: 26) OR [V9T]MCP1(9-76) (SEQ ID NO: 29). The polynucleotides of the present invention may be in the form of RNA or in the form of DNA including synthetic DNA. The DNA may be double-stranded or single-stranded, and if single stranded may be the coding strand or non-coding (anti-sense) strand. The coding sequence which encodes the mature polypeptide may be identical to any coding sequence shown herein or may be a different coding sequence which coding sequence, as a result of the redundancy or degeneracy of the genetic code, encodes the same, mature polypeptides. The polynucleotides which encode the mature polypeptide may include: only the coding sequence for the mature polypeptide; the coding sequence for the mature polypeptide and additional coding sequence such as a leader sequence; and optionally non-coding sequence 5' and/or 3' of the coding sequence for the mature polypeptide. Thus, the term "polynucleotide sequence encoding a protein selected from [V9A]MCP1(9-76) (SEQ ID NO: 9), [V9G]MCP1(9-76) (SEQ ID NO: 26) or 76) (SEQ ID NO: 29)" encompasses a polynucleotide which includes only coding sequence for the polypeptide as well as a polynucleotide which includes additional coding and/or non-coding sequence. Examples of DNA sequences which encode [V9A]MCP1(9-76) (SEQ ID NO: 9), [V9G] MCP1(9-76) (SEQ ID NO: 26) and [V9T]MCP1(9-76) (SEQ ID NO: 29) are set out in SEQ ID NO: 8, 25 and 28 respectively.

In this specification amino acid analogues of specific amino acid sequences are contemplated which retain the relevant biological properties of a component of the invention but differ in sequence by one or more conservative amino acid substitutions, deletions or additions. However the specifically listed amino acid sequences are preferred and analogues should preferably be modified at corresponding positions after position 35 of MCP-1. Truncation at the C-terminus is also contemplated, preferably at corresponding positions after position 52 of MCP-1. Typical conservative amino acid substitutions are tabulated below.

| CONSERVATIVE SUBSTITUTIONS | | |
|---|---|---|
| Initial Amino Acid | Suitable Substitutions | Preferred Substitutions |
| Ala (A) | Val; Leu; Ile; Ser | Ser |
| Arg (R) | Lys; Gln; Asn | Lys |
| Asn (N) | Gln; His; Lys; Arg; Ser; Ala | Gln |
| Asp (D) | Glu; Asn | Glu |
| Cys (C) | Ser; Ala | Ser |
| Gln (Q) | Asn; Met; Leu | Asn |
| Glu (E) | Asp; Gln | Asp |
| Gly (G) | Pro | Pro |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Gly | Gly |
| Ser (S) | Thr; Ala | Thr |
| Thr (T) | Ser; Val; Ile | Ser |
| Trp (W) | Tyr | Tyr |
| Tyr (Y) | Trp; Phe; Thr; Ser | Phe |
| Val (V) | Ile; Leu; Met; Phe; Ala; Thr; Norleucine | Leu |

In this specification nucleic acid variations (deletions, substitutions and additions) of specific nucleic acid sequences are contemplated which retain the ability to hybridise under stringent conditions to the specific sequence in question. Stringent conditions are defined as 6×SSC, 0.1% SDS at 60° C. for 5 minutes. However specifically listed nucleic acid sequences are preferred. It is contemplated that peptide nucleic acid may be an acceptable equivalent of polynucleotide sequences, at least for purposes that do not require translation into protein (Wittung (1994) Nature 368, 561).

According to another aspect of the invention there is provided a vector comprising a polynucleotide sequence encoding a protein selected from [V9A]MCP1(9-76) (SEQ ID NO: 9), [V9G]MCP1(9-76) (SEQ ID NO: 26) or [V9T] MCP1(9-76) (SEQ ID NO: 29). Preferably the vector is an expression vector, more preferably the vector is for use in *E. coli*, especially designed for intracellular expression in *E. coli*. Intracellular expression in *E. coli* can be in soluble form and/or insoluble form. If expressed in insoluble form, for example as inclusion bodies, the protein can be solubilised/refolded by conventional techniques. Expression as inclusion bodies is especially preferred. An especially preferred vector is pZT7#3.3 comprising a polynucleotide sequence encoding aprotein selected from [V9A]MCP1(9-76) (SEQ ID NO: 9), [V9G]MCP1(9-76) (SEQ ID NO: 26) or [V9T] MCP1(9-76) (SEQ ID NO: 29).

Useful expression vectors for bacterial use are constructed by inserting a structural DNA sequence encoding a desired protein together with suitable translation, initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli*. As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well known to those skilled in the art.

According to another aspect of the invention there is provided a host cell comprising a vector as described herein. Preferably the host is *E. coli*.

According to another aspect of the invention there is provided a method of making a protein selected from [V9A]MCP1(9-76) (SEQ ID NO: 9), [V9G]MCP1(9-76) (SEQ ID NO: 26) or [V9T]MCP1(9-76) (SEQ ID NO: 29) which comprises culture of a host as described herein in a culture medium under conditions for expression of the protein and optionally at least partially purifying the protein.

According to another aspect of the present invention there is provided a pharmaceutical composition comprising a protein of the invention described herein in association with a pharmaceutically-acceptable diluent or carrier, optionally in a form suitable for intravenous administration.

According to another aspect of the present invention there is provided a protein as described herein for use as a medicament.

According to another aspect of the present invention there is provided use of a protein as described herein for preparation of a medicament for treatment of inflammatory diseases.

It will be appreciated that the dose and dosage regimen will depend upon the particular effector moiety employed, the population of the target cell and the patient's history. The dose of the protein administered will typically be in the range 0.1 to 10 mg/kg of patient weight.

The proteins of the present invention will normally be administered in the form of a pharmaceutical composition. Thus according to the present invention there is also provided a pharmaceutical compostion which comprises a protein (as defined herein) in association with a pharmaceutically-acceptable diluent or carrier. An example of such a formulation is given herein in Example 5.

Pharmaceutical compositions of the present invention may be formulated in a variety of dosage forms. Generally, the proteins of the present invention will be administered parenterally, preferably intravenously. A particular parenteral pharmaceutical composition is one which is formulated in a unit dosage form which is suitable for administration by injection. A parenteral composition is preferably a solution in isotonic saline or isotonic dextrose, buffered if necessary to a pH of 5 to 9.

Alternatively, the parenteral composition may be one designed for slow release in which case the amount of protein per unit dose is in general greater than that required when a conventional injectable formulation is used. A preferred slow release formulation is a continuous release formulation, for example a fomulation of the type described in European Patent Specification No. 58481. A preferred slow release parenteral formulation contains from 20 to 150 mg of polypeptide per unit dose. Systemic delivery of peptides and proteins is described in Banga et al. (1988), Int. J. Therapeutics 48: 15–50.

Topical administration is also contemplated e.g. for treatment of psoriasis and also administration by inhalation e.g. for treatment of IPF or asthma.

Particularly suitable compositions comprise a solution, emulsion or suspension of the protein in association with a pharmaceutically acceptable parenteral carrier or diluent. Suitable carriers or diluents include aqueous vehicles, for example water or saline, and non-aqueous vehicles, for example fixed oils or liposoines. The compositions may include agents which enhance the stability of the protein in the composition. For example, the composition may include a buffer. The concentration of the protein will vary, but in general, the composition of the invention will normally be administered such that a daily parenteral dose, will be about 10–300 mg for a 70 kg human.

For further information on Formulation the reader is referred to Chapter 25.2 in Volume 5 of Comprehensive Medicinal Chemistry (Corwin Hansch; Chairman of Editorial Board), Pergamon Press 1990. For further information on Routes of Administration and Dosage Regimes the reader is referred to Chapter 25.3 in Volume 5 of Comprehensive Medicinal Chemistry (Corwin Hansch; Chairman of Editorial Board). Pergarnon Press 1990.

According to a further aspect of the present invention there is provided a protein of the invention for use as a medicament.

According to a further aspect of the present invention there is provided use of a protein of the invention in preparation of a medicament for antagonising an MCP-1 mediated effect in a mammal, especially man. Particular MCP-1 mediated effects include inflammatory diseases, especially rheumatoid arthritis, multiple sclerosis and atherosclerosis.

According to a further aspect of the present invention there is provided a method for antagonising an MCP-1 mediated effect in a mammal, such as man, in need of such treatment, which comprises administering to said mammal an effective amount of a pharmaceutical composition of the invention.

Amino acid nomenclature is set out below.

| | | |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Pyroglutamic acid | pGlu | |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any Amino Acid | Xaa | X |

Abbreviations used herein include:

| | |
|---|---|
| ATCC | American Type Culture Collection, Rockville, USA. |
| b.p. | base pair |
| BCA | bicinchroninic acid, (used, with copper sulphate, to assay protein) |
| BPB | bromophenol blue |
| DAB | substrate 3,3'-diaminobenzidine tetrahydrochloride |
| DEPC | diethylpyrocarbonate |
| DMEM | Dulbecco's modified Eagle's medium |
| DTT | dithiothreitol |
| ECACC | European Collection of Animal Cell Cultures |
| EDTA | ethylenediaminetetraacetic acid |
| EGTA | ethylenebis(oxyethylenenitrilo)tetraacetic acid |
| EIA | enzyme immunoassay |
| ELISA | enzyme linked immunosorbent assay |
| FCS | foetal calf serum |
| HBSS | Hank's Balanced Salt Solution |
| HEPES | 4-(2-hydroxyethyl)-1-piperazineethanesulfonic acid |
| rpHPLC | reverse phase high pressure liquid chromatography |
| HRPO | horse radish peroxidase |
| IPF | Idiopathic Pulmonary Fibrosis |
| MCP-1 | Monocyte Chemoattractant Protein-1 |
| NCIMB | National Collections of Industrial and Marine Bacteria |
| PBS | phosphate buffered saline |
| PCR | polymerase chain reaction |
| PMSF | phenylmethylsulfonylfluoride |
| SDS-PAGE | sodium dodecyl sulphate-polyacrylamide gel electrophoresis |
| SSC | salt sodium citrate |
| TBS | Tris-buffered Saline |
| Temed | N,N,N',N'-tetramethylethylenediamine |
| Tris | Tris(hydroxymethyl)aminomethane |

The following Figures are cited in the text below.

Figure 1:
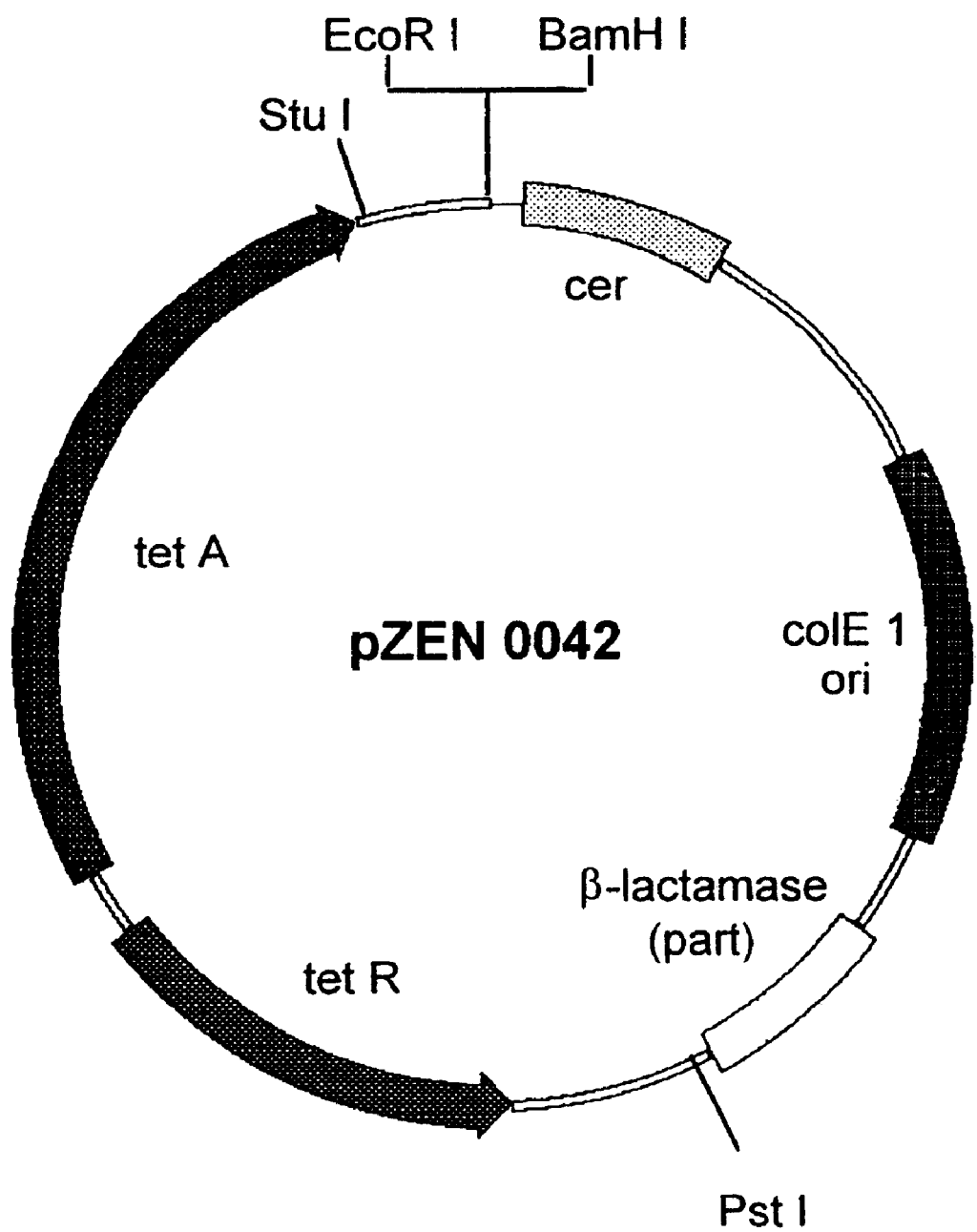
FIG. 1 shows the pZEN0042 plasmid.

The invention is illustrated below with reference to the following non-limiting Examples. Temperatures are in degrees Celsius and the general details set out below have been used except where indicated otherwise.

DNA is recovered and purified by use of GENECLEAN™ II kit (Stratech Scientific Ltd. or Bio 101 Inc.). The kit contains: 1) 6M sodium iodide; 2) a concentrated solution of sodium chloride, Tris and EDTA for making a sodium chloride/ethanol/water wash; 3) Glassmilk—a 1.5 ml vial containing 1.25 ml of a suspension of a specially formulated silica matrix in water. Thlis is a technique for DNA purification based on the method of Vogelstein and Gillespie published in Proceedings of the National Academy of Sciences USA (1979) Vol 76, p 615. Briefly, the kit procedure is as follows. To 1 volume of gel slice is added 3 volumes of sodium iodide solution from the kit. The agarose is melted by heating the mix at 55° for 10 min then Glassmilk (5–10 ml) is added, mixed well and left to stand for 10 min at ambient temperature. The glassmilk is spun down and washed 3 times with NEW WASH™ (0.5 ml) from the kit. The wash buffer is removed from the Glassmilk which is to dry in air. The DNA is eluted by incubating the dried Glassmilk with water (5-10 ml) at 55° for 5–10 min. The aqueous supernatant containing the eluted DNA is recovered by centrifugation. The elution step can be repeated and supernatants pooled.

Competent *E. coli* DH5α cells were obtained from Life Technologies Ltd (MAX™ efficiency DH5α competent cells).

Mini-preparations of double stranded plasmid DNA were made using the RPM™ DNA preparation kit from Bio 101 Inc. (cat. No 2070-400) or a similar product—the kit contains alkaline lysis solution to liberate plasmid DNA from bacterial cells and glassmilk in a spinfilter to adsorb liberated DNA which is then eluted with sterile water or 10 mM Tris-HCl, 1 mM EDTA, pH 7.5.

AMPLITAQ™, available from Perkin-Elmer Cetus, is used as the source of thermostable DNA polymerase.

Binding Buffer is 50 mM HEPES, 1 mM $CaCl_2$, 5 mM $MgCl_2$, 0.5% foetal calf serum, adjusted to pH 7.2 with 1 M NaOH.

L-broth is tryptone (10 g/l, Difco), yeast extract (5 g/l, Difco), sodium chloride (5g/l), pH 7.2.

Lysis Buffer is 40 mM sodium phosphate, 1 mM EDTA, 1 mM PMSF and 1 µM leupeptin, pH 7.4.

Wash Buffer is 40 mM sodium phosphate and 1 mM EDTA, pH 7.4.

Solubilisation Buffer is 40 mM sodium phosphate, 1 mM EDTA, 5 mM DTT and 8 M urea, pH 8.0.

Refolding Buffer is 20 mM sodium phosphate, pH 7.5.

Non-Essential Amino Acids (100× concentrate) is: L-Alanine, 890 mg/l; L-Asparagine, 1320 mg/l; L-Aspartic acid, 1330 mg/l; L-Glutamic acid, 1470 nmg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt): 5000 units/ml; Streptomycin sulphate, 5000 µg/ml.

*E. coli* expression strain MSD2052 is *E. coli* BL21 (DE3), available from Novagen, catalogue number 69387-1.

*E. coli* strain MSD 101 is strain W3110 available from Genetic Stock Centre, Yale University.

*E. coli* strain MSD 213 is *E. coli* strain MC1000, see Silhavy, T. J., Berman, M. L., and Enquist, L. W. 1984, Experiments with Gene Fusions, Cold Spring Harbor Laboratory, Cold Spring Harbor, N.Y. and is available from the CGSC at Yale, strain no. CGSC 6647. See also Casadaban, M. (1980) J. Mol. Biol. 138:179.

*E. coli* strain MSD 525 is *E. coli* strain MC1061 see Huynh, T. V., Young, R. A., and Davis, R. W. 1985 in DNA Cloning (D. M. Glover ed.), Vol 1, 56–110, IRL Press, Oxford England, and is avialable from the CGSC at Yale, strain no CGSC 6649. See also Casadaban, M. (1980) J. Mol. Biol. 138:179.

*E. coli* strain MSD 1924 is an ara minus derivative of *E. coli* strain C600 (available as CGSC 3004).

Human monocytic cell line THP-1 cells are available from ATCC, accession number ATCC TIB-202.

Hank's Balanced Salt Solution (HBSS) was obtained from Gibco; see Proc. Soc. Exp. Biol. Med., 1949, 71, 196.

Synthetic cell culture medium, RPMI 1640 was obtained from Gibco; it contains inorganic salts [$Ca(NO_3)_2.4H_2O$ 100 mg/l; KCl 400 mg/l; $MgSO_4.7H_2O$ 100 mg/l NaCl 6000 mg/l; $NaHCO_3$ 2000 mg/l & $Na_2HPO_4$ (anhyd) 800 mg/l], D-Glucose 2000 mg/l, reduced glutathione 1 mg/l, amino acids and vitamins.

FURA-2/AM is 1-[2-(5-carboxyoxazol-2-yl)-6-aminobenzofuran-5-oxy]-2-(2'-amino-5'-methylphenoxy)-ethane-N,N,N',N'-tetraacetic acid pentaacetoxymethyl ester and was obtained from Molecular Probes, Eugene, Ore., USA.

Calcein AM is Glycine, N,N'-[[3',6'-bis(acetyloxy)-3-oxospiro[isobeizofuran-1(3H),9 '-[9H]xanthene]-2',7'-diyl] bis(methylene)]bis[N-[2-[(acetyloxy)methoxy]-2-oxoethyl 1]]-, bis[(acetyloxy)methyl]ester, and was obtained from Molecular Probes, Eugene, Oreg., USA.

General molecular biology procedures can be followed from any of the methods described in "Molecular Cloning—A Laboratory Manual" Second Edition. Sambrook, Fritsch and Maniatis (Cold Spring Harbor Laboratory, 1989).

EXAMPLE 1

Intracellular Expression of [V9A]MCP1(9-76) (SEQ ID NO: 9) in *E. coli*

[V9A]MCP1(9-76) (SEQ ID NO: 9) was generated by PCR from MCP-1(9-76) (see Comparative Example 1) using a 5' PCR primer (SEQ ID NO: 1) which changes the valine at position 9 to an alanine and incorporates an NdeI site, and a 3' PCR primer (SEQ ID NO: 2) which incorporates a BamHI site. The resulting PCR product was was sub-cloned as an NdeI-BamHI fragment into the vector pZT7#3.3 (see Reference Example 2) to generate pZT7#3.3/[V9A]MCP1 (9-76). This construct was used to transform *E. coli* DH5α. DNA was prepared from the resulting recombinant *E. coli* and a clone with the correct sequence was identified by DNA sequencing. pZT7#3.3/[V9A]MCP1(9-76) DNA was used to transform the *E. coli* expression strain MSD 2052.

A seeder culture of the *E. coli* expression strain MSD2052 was incubated in 100 ml L-broth containing glucose (1 g/l) overnight at 370, shaking at 300 rpm. The following day this culture was inoculated to an optical density of 0.1 in the appropriate volume (e.g. 100 ml) of L-broth containing glucose (1 g/l), lactose (1 g/l), tetracycline (15 mg/l) and incubated at 37°, shaking at 300 rpm for 4–6 h.

*E. coli* cell paste containing [V9A]MCP1(9-76) (SEQ ID NO: 9) was resuspended in Lysis Buffer at 4° using a homogeniser (Kinematica Polytron). The cells were then lysed by recirculation through a homogeniser (Manton Gaulin) at 4000 psi at 4°. The resulting solution was then centrifuged for 1 hour at 7300 g. The supernatant was aspirated and the pellet containing [V9A]MCP1(9-76) (SEQ ID NO: 9) was recovered. This pellet was then washed twice by resuspension in Wash Buffer at 4°, followed by centrifugation for 1 hour at 7300 g. The washed pellet was resuspended in Solubilisation Buffer at 4° and stirred overnight. The solution was then centrifuged at 27,500 g for 45 minutes at 4°. The supernatant, containing the solubilised [V9A] MCP1(9-76) (SEQ ID NO: 9), was aspirated. The resulting pellet was washed twice by resuspension in Solubilisation Buffer at 4°, followed by centrifugation at 27,5000 g for 45 minutes at 4°. After each wash step the supernatant was aspirated. The supernatant from the solubilisation step and the supernatants from the two wash steps were combined and passed through a 0.45 μm filter. The resulting pool was then loaded on to a cation ion exchange column (S Sepharose™ Fast Flow, Pharmacia) which had been pre-equilibrated with Solubilisation Buffer. The column was monitored at 280 nm and washed with Solubilisation Buffer until the trace returned to baseline. The column was then step eluted using Solubilisation Buffer containing 1 M sodium chloride and fractions were collected. The fractions were then analysed by SDS PAGE gels and those containing [V9A]MCP1(9-76) (SEQ ID NO: 9) were pooled. The pool was diluted with Solubilisation Buffer to give a final $A_{280\,nm}$ of 1. The pool was then dialysed against Refolding Buffer at 4° to remove the urea and DTT. The dialysate was then centrifuged at 27,500 g at 4° for 1 hour. The supernatant was aspirated and loaded onto a hydroxyapatite column (Biorad) which had been pre-equilibrated with Refolding Buffer. The column was monitored at 280 nm and washed with Refolding Buffer until the trace returned to baseline. The column was then eluted with a gradient over 20 column volumes of 0.4 M sodium phosphate, pH 7.5, and fractions were collected. The fractions were then analysed by SDS PAGE gels and those containing [V9A]MCP1(9-76) (SEQ ID NO: 9) were pooled and filtered through a 0.22 μm filter. The resulting [V9A]MCP1(9-76) (SEQ ID NO: 9) was >95% pure as measured by Coomassie stained SDS PAGE gels.

Analysis by Edman degradation and electrospray mass spectrometry showed that the N-terminal methionine had been processed, leaving alanine as the only detectable N-terminal amino acid. This was confirmed by rpHPLC where a single peak for [V9A]MCP1 (9-76) (SEQ ID NO: 9), with no evidence of a second peak for the protein species where the initiating methionine had been retained.

EXAMPPL 2

Biological Activity of [V9A]MCP1(9-76) (SEQ ID NO: 9) and other MCP-1 Analogues

Biological activity was determined using the assay methods described in Reference Example 1 below. Results are presented in the Table below.

TABLE

Inhibition of hMCP-1 Mediated Activities (IC$_{50}$)

| Product | Receptor-binding | Chemotaxis | Calcium flux |
| --- | --- | --- | --- |
| MCP1(9-76) (SEQ ID NO: 30) | 1.9 nM* | 12 nM*** | 45 nM*** |
| [V9A]MCP1(9-76) (SEQ ID NO: 9) | 2.5 nM* | 23 nM*** | 109 nM*** |
| [V9G]MCP1(9-76) (SEQ ID NO: 26) | 3.2 nM** | 10.9 nM*** | not done |
| [V9T]MCP1(9-76) (SEQ ID NO: 29) | 2.0 nM** | 21 nM*** | not done |

TABLE-continued

Inhibition of hMCP-1 Mediated Activities (IC$_{50}$)

| Product | Receptor-binding | Chemotaxis | Calcium flux |
| --- | --- | --- | --- |
| Met-MCP1(9-76) (SEQ ID NO: 31) | 3.2 nM | not done | not done |
| pGlu-MCP1(9-76) (SEQ ID NO: 32) | 2.6 nM | not done | 117 nM |

*mean of 18 independent assays
**mean of 8 independent assays
***mean of 3 independent assays Other data was the result of at least 2 independent assays.

These results demonstrate that, within experimental error, all the analogues tested have a similar potency. [V9A]MCP1 (9-76) (SEQ ID NO: 9) in these assays is indistinguishable from the known antagonist pGlu-MCP1(9-76) descibed by Barratt Rollins.

EXAMPLE 3

Intracellular Expression of [V9G]MCP1(9-76) (SEQ ID NO: 26) in E. coli

[V9G]MCP1(9-76) was prepared using methodology as described in Example 1 but substituting a 5' PCR primer of SEQ ID NO: 24, in lieu of the 5' PCR primer of SEQ ID NO: 1, which changes the valine at position 9 to a glycine.

The resulting [V9G]MCP1(9-76) (SEQ ID NO: 26) was >95% pure as measured by Coomassie stained SDS PAGE gels. Analysis by Edman degradation showed that there was detection of both methionine and glycine on the first cycle. Based on the recovery of methionine and glycine on the first cycle, approximately 5% of the protein had retained the initiating methionine. This was confirmed by electrospray mass spectrometry where both protein species could be detected. It is envisaged that the amount of N-terminal methionine could be further reduced by suitable methods, such as, for example, using different host strains, modulation or optimisation of the fermentation and induction conditions and/or increasing the amount of methionine aminopeptidase (MAP) by, for example, co-overexpressing recombinant MAP.

EXAMPLE 4

Intracellular Expression of [V9T]MCP1(9-76) (SEQ ID NO: 29) in E. coli

The resulting [V9T]MCP1(9-76) (SEQ ID NO: 29) was >95% pure as measured by Coomassie stained SDS PAGE gels. Analysis by Edman degradation showed that there was detection of both methionine and threonine on the first cycle. Based on the recovery of methionine and threonine on the first cycle, approximately 10% of the protein had retained the initiating methionine. This was confirmed by electrospray mass spectrometry where both protein species could be detected. It is envisaged that the amount of N-terminal methionine could be further reduced by suitable methods, such as, for example, using different host strains, modulation or optimisation of the fermentation and induction conditions and/or increasing the amount of methionine aminopeptidase (MAP) by, for example, co-overexpressing recombinant MAP.

EXAMPLE 5

Pharmaceutical Composition

The following illustrates a representative pharmaceutical dosage form containing a protein of the invention which may be used for therapy.

Injectable Solution

A sterile aqueous solution, for injection, containing per ml of solution:

| [V9A]MCP1(9-76)(SEQ ID NO: 9) | 5.0 mg |
|---|---|
| Sodium acetate trihydrate | 6.8 mg |
| Sodium chloride | 7.2 mg |
| Tween 20 | 0.05 mg |

A typical daily dose of protein for adult humans is 30–300 mg.

COMPARATIVE EXAMPLE 1

Intracellular Expression of MCP1(9-76) (SEQ ID NO: 30) in E. coli

MCP1(9-76) was generated by PCR using a combination of two overlapping oligonucleotides which represent the entire MCP-1 coding sequence, with each codon modified for preferred E. coli codon usage (SEQ ID NO: 3 and SEQ ID NO: 4), in combination with 5' PCR primer (SEQ ID NO: 5) which incorporates an NdeI site, and a 3' PCR primer (SEQ ID NO: 2) which incorporates a BamHI site. The resulting PCR product was was sub-cloned as an NdeI-BamHI fragment into the vector pZT7#3.3 (see Reference Example 2) to generate pZT7#3.3/MCP1(9-76). This construct was used to transform E. coli DH5α. DNA was prepared from the resulting recombinant E. coli and a clone with the correct sequence was identified by DNA sequencing. pZT7#3.3/[V9A]MCP1(9-76) DNA was used to transform the E. coil expression strain MSD 2052.

A seeder culture of the E. coli expression strain MSD2052 was incubated in 100 ml L-broth containing glucose (1 g/l) overnight at 37°, shaking at 300 rpm. The following day this culture was inoculated to an optical density of 0.1 in the appropriate volume (e.g. 100 ml) of L-broth containing glucose (1 g/l), lactose (1 g/l), tetracycline (15 mg/l) and incubated at 37°, shaking at 300 rpm for 4–6 h.

E. coli cell paste containing Met(+/−)-MCP1(9-76) was resuspended in Lysis Buffer at 4°. To this solution was added 1 µg/ml of lysozme and the solution was then gently stirred on ice for 30 minutes. The cells were then lysed by sonication and the resulting solution was then centrifuged for 1 hour at 7300 g. The supernatant was aspirated and the pellet containing Met(+/−)-MCP1(9-76) was recovered. The pellet was resuspended in Solubilisation Buffer at 4° and stirred overnight. The solution was then centrifuged at 27,500 g for 45 minutes at 4°. The supernatant, containing the solubilised Met(+/−)-MCP1(9-76), was aspirated and passed through a 0.45 µm filter. The solubilisation supernatant was then loaded on to a cation exchange column (S Sepharose™ Fast Flow, Pharmacia) which had been pre-equilibrated with Solubilisation Buffer. The column was monitored at 280 nm and washed with Solubilisation Buffer until the trace returned to baseline. The column was then step eluted using Solubilisation Buffer containing 1 M sodium chloride and fractions were collected. The fractions were then analysed by SDS PAGE gels and those containing Met(+/−)-MCP1 (9-76) were pooled. The pool was diluted with Solubilisation Buffer to give a final $A_{280\ nm}$ of 1. The pool was then dialysed against Refolding Buffer at 4° to remove the urea and DTT. The dialysate was then centrifuged at 27,500 g at 4° for 1 hour. The supernatant was aspirated and loaded onto a cation exchange column (Mono S™, Pharmacia) which had been pre-equilibrated into Refolding Buffer. The column was monitored at 280 nm. The column was washed with Refolding Buffer until the trace returned to baseline. The column was then eluted with a gradient of 1 M sodium chloride in Refolding Buffer, and fractions were collected. The fractions were then analysed by SDS PAGE gels and those containing Met(+/−)-MCP1(9-76) were pooled and 0.22 µm filtered. The resulting Met(+/−)-MCP1(9-76) was >95% pure as measured by Coomassie stained SDS PAGE gels.

Analysis by Edman degradation and electrospray mass spectrometry showed that only approximately 50% of the N-terminal methionine had been processed, leaving a mixture of methionine and valine as the N-terminal amino acid. This was confirmed by rpHPLC whether two peaks were obtained. Electrospray mass spectrometry showed that the first peak was MCP-1(9-76) (SEQ ID NO: 30) and the second later eluting peak was Met-MCP1(9-76) (SEQ ID NO: 31).

COMPARATIVE EXAMPLE 2

Secretory Expression of MCP-1(9-76) (SEQ ID NO: 30) in E. coli

An MCP1(9-76) expression construct suitable for secretion in E. coli was generated by PCR from MCP-1 (9-76) (see Comparative Example 1) using a 5' PCR primer (SEQ ID NO: 6) which enables fusion of the amino acid at position 9 (Val) with a secretory leader sequence in the vector pAG170 using a NcoI site, and a 3' PCR primer (SEQ ID NO: 7) incorporating an XhoI site. The resulting PCR product was was sub cloned as a NcoI-XhoI fragment into the vector pAG170 to generate pAG170/sMCP1(9-76). This construct was used to transform E. coli DH5α. DNA was prepared from the resulting recombinant E. coli and a clone with the correct sequence was identified by DNA sequencing. pAG 170/sMCP1 (9-76) DNA was used to transform a suitable E. coli expression strain.

A seeder culture of the E. coli expression strain MSD525, MSD213 or MSD 1924 was incubated in 100 ml L-broth containing glucose (1 g/l) overnight at 37°. shaking at 300 rpm. The following day this culture was re-inoculated to an optical density of 0.1 in the appropriate volume of L-broth containing glucose (1 g/l). lactose (1 g/l) and incubated at 37°, shaking at 300 rpm until the culture reached an optical density of 0.5. At this point, arabinose was added to the culture to a final concentration of 1% and incubated for a further for 4 h at 37° with shaking at 300 rpm.

The accumulation of MCP-1(9-76) (SEQ ID NO: 30) was analysed by Coomassie stained SDS PAGE gels of a sample of whole E. coli from the fermentation. By this analysis no significant band, >1% total cell protein, could be seen running at the molecular weight expected for MCP-1(9-76) (SEQ ID NO: 30). To confirm this E. coli cell paste from the MCP-1(9-76) (SEQ ID NO: 30) fermentation was resuspended in Lysis Buffer at 4°. To this solution was added 1 µg/ml of lysozme and the solution was then stirred gently for 30 minutes on ice. The cells were then lysed by sonication. The resulting solution was then centrifuged for 1 hour at 7300 g. The resulting supernatant and pellet were then analysed by Coomassie stained SDS PAGE gels. By this analysis, no significant band was visible at the molecular weight expected for MCP-1(9-76) (SEQ ID NO: 30) in either the pellet or the supernatant fractions. This analysis showed that MCP-1(9-76) (SEQ ID NO: 30) did not accumulate at significant levels when expressed and secreted into the periplasm of E. coli.

REFERENCE EXAMPLE 1

Assays for hMCP-1 and hMCP-1 Antagonists
a) hMCP-1 Receptor-binding Assay
 i) Cloning and expression of hMCP-1 receptor The MCP-1 receptor B (CCR2B) cDNA was cloned by PCR from THP-1 cell RNA using oligonucleotide primers based on the published MCP-1 receptor sequences (Charo et al., 1994, Proc. Natl. Acad. Sci. USA, 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (InVitrogen) to generate pCDNA3/CCR2A and pCDNA3/CCR2B respectively.

Linearised pCDNA3/CCR2B DNA was transfected into CHO-K1 cells by calcium phosphate precipitation (Wigler et al., 1979, Cell, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, Prot. Express. Purific., 6, 134). CHO-K1 clone 7 (CHO-CCR2B) was identified as the highest MCP-1 receptor B expressor.

ii) Preparation of Membrane Fragments

CHO-CCR2B cells were grown in DMEM supplemented with 10% foetal calf serum, 2 mM glutamine, 1×Non-Essential Amino Acids, 1×Hypoxanthine and Thymidine Supplement and Penicillin-Streptomycin (at 50 µg streptomycinlml, Gibco BRL). Membrane fragments were prepared using cell lysis/differential centrifugation methods as described previously (Siciliano el al., 1990, J. Biol. Chem., 265, 19658). Protein concentration was estimated by BCA protein assay (Pierce, Rockford, Ill.) according to the manufacturer's instructions.

iii) Assay $^{125}$I MCP-1 was prepared using Bolton and Hunter conjugation (Bolton et al., 1973, Biochem. J., 133, 529; Amersham International plc]. Equilibrium binding assays were carried out using the method of Ernst et al., 1994, J. Immunol., 152, 3541. Briefly, varying amounts of $^{125}$I-labeled MCP-1 were added to 10 µg of purified CHO-CCR2B cell membranes in 100 µl of Binding Buffer. After 1 hour incubation at room temperature the binding reaction mixtures were filtered and washed 5 times through a plate washer (Packard Harvester Filtermate™ 196). Scintillation fluid (25 µl, Microscint™-20, a high efficiency liquid scintillation counting cocktail for aqueous samples) was added to each well and the plate was covered with plate sealer and counted (Packard Top Count™). Cold competition studies were performed as above using 100 pM $^{125}$I-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Potential antagonists (10 µl) were tested in competition with 100 pM labeled MCP-1 over a concentration range (0.1–100 nM) in duplicate using eight point dose-response curves and $IC_{50}$ concentrations were calculated.

b) MCP-1 Mediated Calcium Flux in THP-1 Cells

The human monocytic cell line THP-1 was grown in a synthetic cell culture medium RPMI 1640 supplemented with 10% foetal calf serum, 2 mM glutamine and Penicillin-Streptomycin (at 50 µg streptomycin/ml, Gibco BRL). THP-1 cells were washed in HBSS (lacking $Ca^{2+}$ and $Mg^{2+}$) +1 mg/ml BSA and resuspended in the same buffer at a density of $3\times10^6$ cells/ml. The cells were then loaded with 1 mM FURA-2/AM for 30 min at 37°, washed twice in HBSS, and resuspended at $1\times10^6$ cells/ml. THP-1 cell suspension (0.9 ml) was added to a 5 ml disposable cuvette containing a magnetic stirrer bar and 2.1 ml of prewarmed (37°) HBSS containing 1 mg/ml BSA, 1 mM $MgCl_2$ and 2 mM $CaCl_2$. The cuvette was placed in a fluorescence spectrophotometer (Perkin Elmer, Norwalk, Conn.) and preincubated for 4 min at 37° with stirring. Fluorescence was recorded over 70 sec and cells were stimulated by addition of hMCP-1 to the cuvette after 10 sec. $[Ca^{2+}]i$ was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give an estimate of cytoplasmic [$Ca^{2+}$ according to the equation:

$$[Ca^{2+}]i = K_d \frac{(R-Rmin)}{(Rmax-R)}(Sf2/Sb2)$$

where the $K_d$ for FURA-2 $Ca^{2+}$ complex at 37° was taken to be 224 nM. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in $[Ca^{2+}]i$ in a specific and dose dependent manner. Dose response curves indicated an approximate $EC_{50}$ of 2 nM. Antagonists were tested by adding them to the cell suspension 10 sec prior to ligand addition and measuring the reduction in the transient rise in $[Ca^{2+}]i$. Antagonists were also checked for lack of agonism by addition in place of hMCP-1.

c) hMCP-1 Mediated Chemotaxis Assay.

In vitro chemotaxis assays were performed using the human monocytic cell line THP-1. The chemoattractant MCP-1 was introduced into a 96-well plate which forms the lower part of a chemotaxis chamber fitted with a PVP-free 5 µm poresize polycarbonate filter membrane (CHEMO TX chamber™ Code 106-5, NeuroProbe, Cabin John, MD. 20818, USA) according to the manufacturer's instructions. A submaximal concentration of MCP-1 (1 nM) was diluted as appropriate in synthetic cell culture medium, HBSS with $Ca^{2+}$ and $Mg^{2+}$ and without Phenol Red (Gibco) plus 0.1% BSA. Peptide antagonists were included in this solution where appropriate. Each dilution was degassed under vacuum for 30 minutes and placed (30 µl) in the lower wells of the chamber. THP-1 cells were fluorescently tagged by incubation in the presence of 5 µM Calcein AM (Molecular Probes) for 45 minutes in the dark. Cells were harvested by centrifuigation and resuspended in HBSS (without Phenol Red) with $Ca^{2+}$, $Mg^{2+}$ and 0.1% BSA. THP-1 cell suspension, 50 µl ($2\times10^5$ cells), was placed on the filter above each well and the unit was incubated at 37° for 2 hours under 5% $CO_2$. At the end of the incubation, cells were washed off the upper face of the filter with phosphate buffered saline, the filter removed from the plate and the number of cells attracted to the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, and significance tests were calculated. MCP-1 induced concentration dependent cell migration with a characteristic biphasic response maximal around 5 nM.

RP4 and the cer stability sequence from plasmid pKS492 in a pAT153 derived background (FIG. 1).

The Table below describes oligonucleotides used in this Example.

TABLE 1

```
PCR primer #1 (lac I 5'-3'); SEQ ID NO:10
GATGCTATAATGCATGACACCATCGAATGGCGCAA PCR primer #2 (lacI 3'-5'); SEQ ID NO:11
CAGTATGCACAGTATGCATTTACATTAATTGCGTTGCGCTC 5'-3' oligomer #3; SEQ ID NO:12
AATTCCAGACATATGGTACCAGTACTCTATACTAGTTGAAGGATCCATGCCTCGAGAAC
GCTGCAGAGCTAAGCTTGACAAGATCTAA 3'-5' oligomer #4: SEQ ID NO:13
GATCTTAGATCTTGTCAAGCTTAGCTCTGCAGCGTTCTCGAGGCATGGATCCTTCAACTA
GTATAGAGTACTGGTACCATATGTCTGG 5'-3' oligomer #5: SEQ ID NO:14
AGCTTAACAAAGCCCGAAAGGAAGCTGAGTTGGCTGCTGCCACCGCTGAGCAATAACT
AGCATAACCCCTTGGGGCCTCTAAACGGGTCTTGAGGGGTTTTTGA 3'-5' oligomer #6: SEQ ID NO:15
GATCTCAAAAAACCCCTCAAGACCCGTTTAGAGGCCCCAAGGGGTTATGCTAGTT
ATTGCTCAGCGGTGGCAGCAGCCAACTCAGCTTCCTTTCGGGCTTTGTTA 5'-3' oligomer #7: SEQ ID NO:16
TCGAGGCATTGTCCTCTTAGTTAAATGGATATAACGAGCCCCTCCTAAGGGCTAATTGC
AGGTTCGATTCCTGCAGGGGACTCCACTGCA 3'-5' oligomer #8: SEQ ID NO:17
GTGGAGTCCCCTGCAGGAATCGAACCTGCAATTAGCCCTTAGGAGGGGCTCGTTATATC
CATTTAACTAAGAGGACAATGCC 5'-3' oligomer #9: SEQ ID NO:18
CCTATTATATTACTAATTAATTGGGGACCCTAGAGGTCCCCTTTTTTATTTTAAAACCAT
GGAACCAACCG 3'-5' oligomer #10: SEQ ID NO:19
AATTCGGTTGGTTCCATGGTTTTAAAATAAAAAAGGGGACCTCTAGGGTCCCCAATTAA
TTAGTAATATAATAGG 5'-3' oligomer #11: SEQ ID NO:20
AATTCCGAAATTAATACGACTCACTATAGGGGAATTGTGAGCGCTCACAATTCCCCTCT
AGAAATAATTTTGTTTAACTTTAAGAAGGAGATATACA 3'-5' oligomer #12: SEQ ID NO:21
TATGTATATCTCCTTCTTAAAGTTAAACAAAATTATTTCTAGAGGGGAATTGTGAQCGC
TCACAATTCCCCTATAGTGAGTCGTATTAATTTCGG 5'-3' oligomer #13: SEQ ID NO:22
CATGGACGTGTTAACAACCAACCGGAATTGTGAGCGCTCACAATTCCATCCAAGA
ACAACCATCCTAGCAACACGGCGGTCCCCG 3'-5' oligomer #14: SEQ ID NO:23
AATTCGGGGACCGCCGTGTTGCTAGGATGGTTGTTCTTGGATGGAATTGTGAGCG
CTCACAATTCCGGTTGGTTGTTAACACGTC
```

REFERENCE EXAMPLE 2

Preparation of Vector pZT7#3.3

Figure 4:
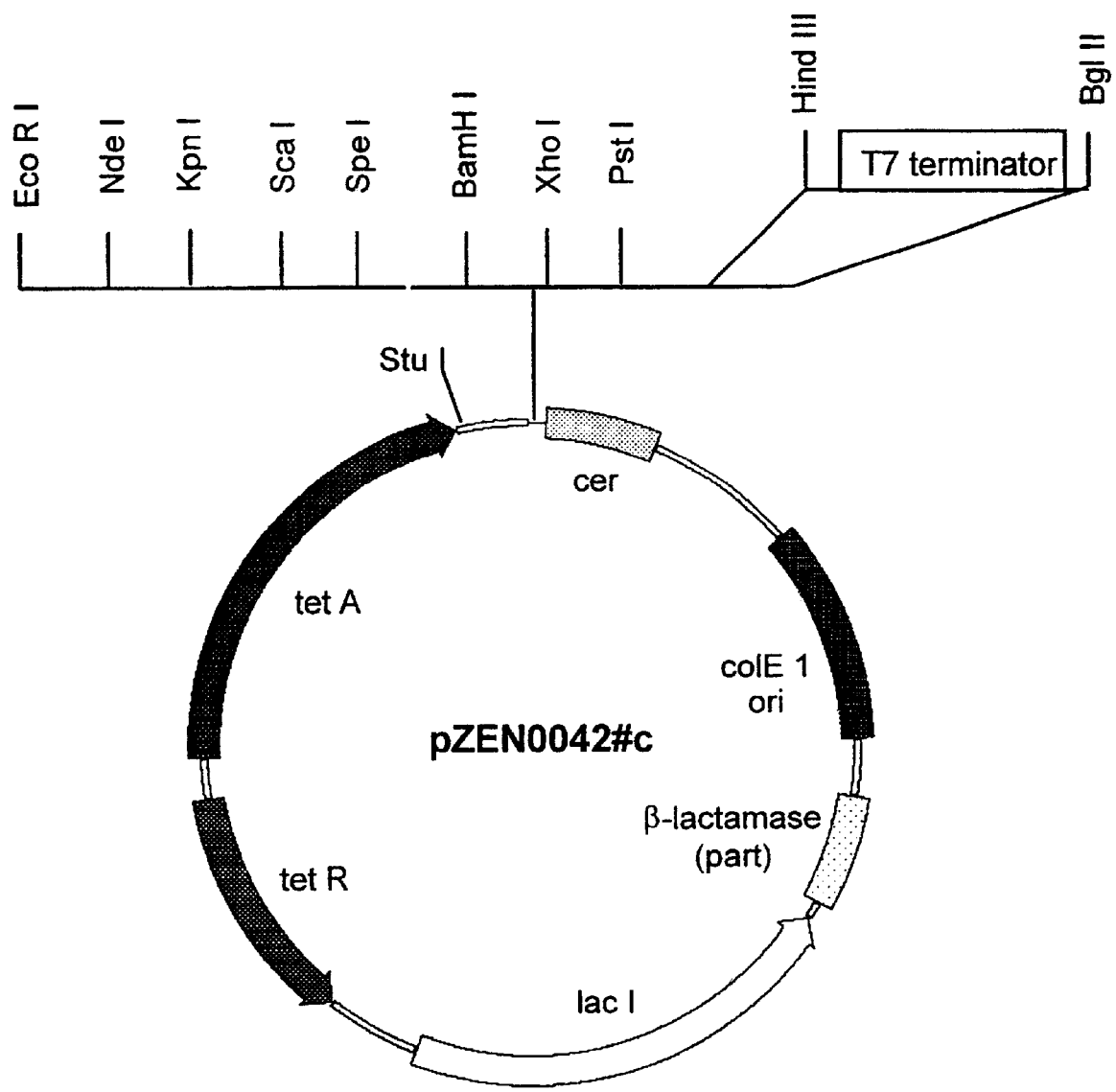
FIG. 4 shows the pZEN0042#c plasmid.

The starting vector for generation of pZT7#3.3 was pZEN0042, described fully (as pICI0042) in European patent application EP 502637 (Imperial Chemical Industries; see FIG. 4 therein). Briefly, this vector contains the tetA/tetR inducible tetracycline resistance sequence from plasmid RP4 and the cer stability sequence from plasmid pKS492 in a pAT153 derived background (FIG. 1).

1(i) Cloning of Lac I

Figure 2:
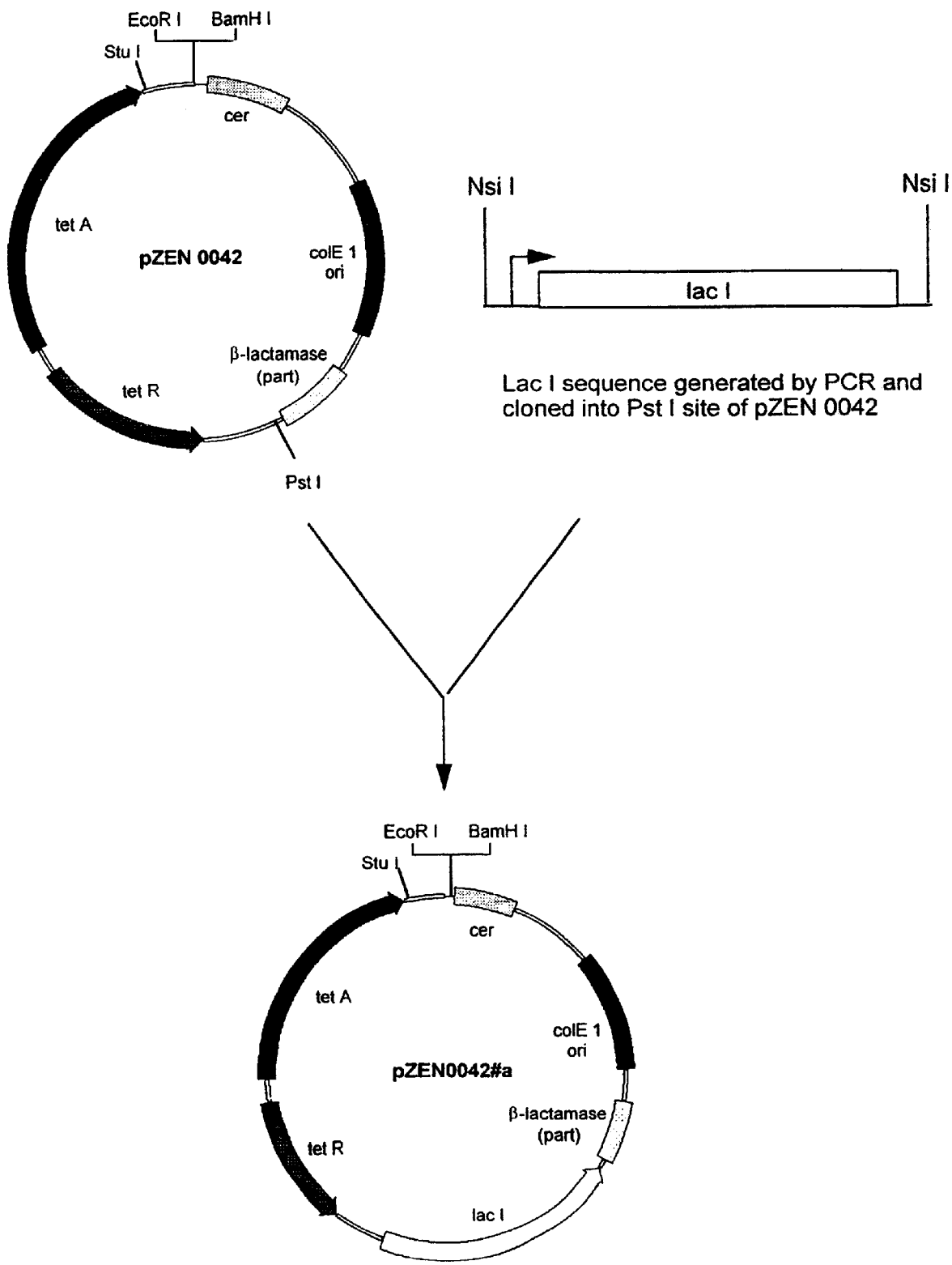
FIG. 2 shows the construction of pZEN0042#a from pZEN0042.

The sequence of lac I including the lac repressor coding sequence and lac I promoter was generated by polyrnerase chain reaction using genomic DNA prepared from E. coli strain MSD 101. Nsi I restriction endonuclease sites were generated at both ends of the sequence by incorporation into the PCR primers #1 and #2 (Table 1). The PCR product obtained was digested with Nsi I and cloned into pZEN0042 at the Pst I site (Pst I and Nsi I have compatible cohesive ends resulting in both sites being destroyed). Both orientations of lac I were obtained. A clone with a correct sequence lac I in the anti-clockwise orientation was identified (pZEN0042#a) (FIG. 2).

(ii) Cloning of Plylinker

A new multiple cloning site was generated in pZEN0042#a to allow subsequent cloning of the T7 expression cassette. This was achieved by digesting pZEN0042#a with EcoR I and BamH I and ligating with annealed, synthetic oligomers #3 and #4 (Table 1).

Figure 3:
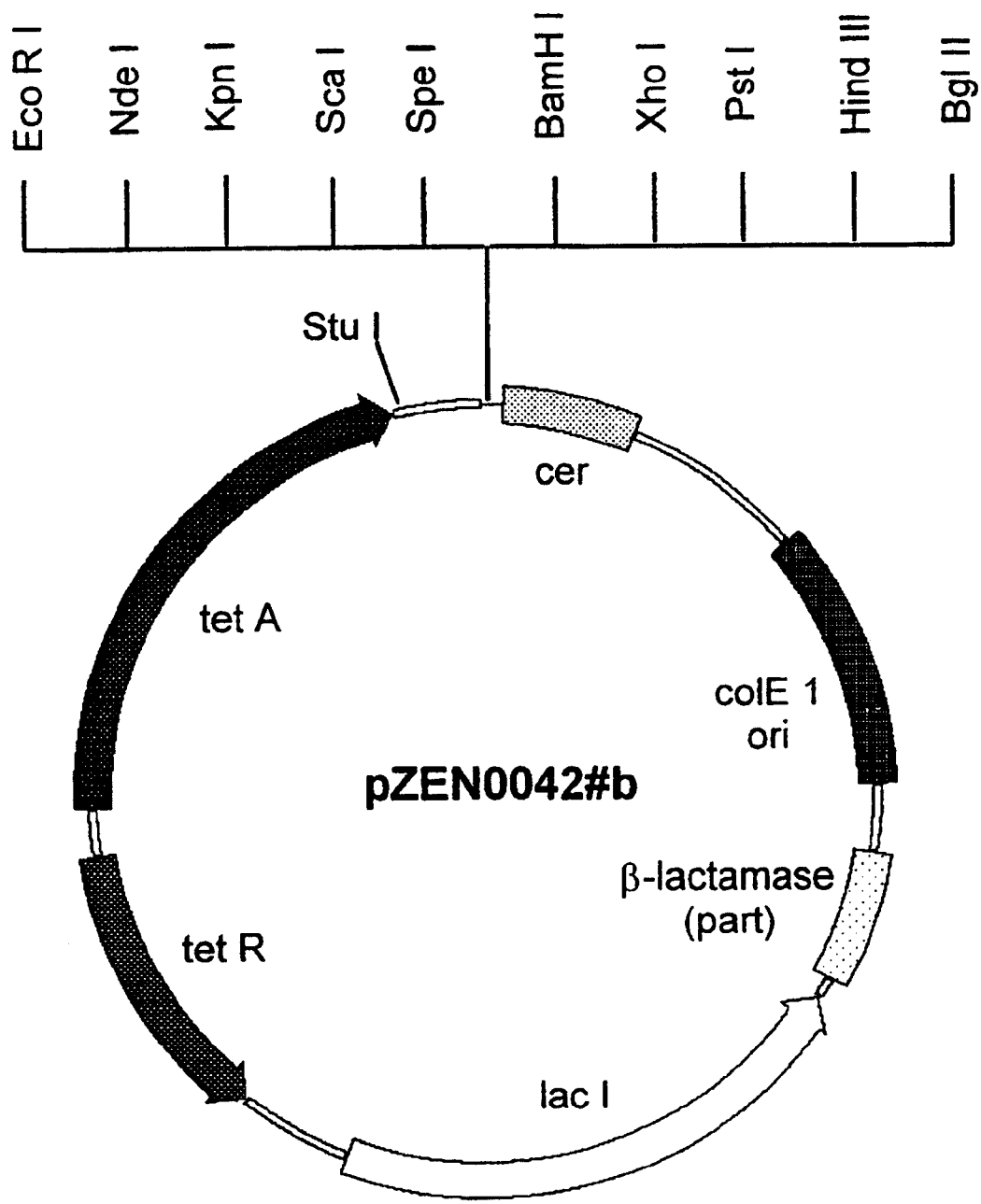
FIG. 3 shows the pZEN0042#b plasmid.

The polylinker of the resulting vector, pZEN0042#b, had the following restriction sites: EcoRI-Nde I-Kpn I-Sca I-Spe I-BamH I-Xho I-Pst I-Hind III-Bgl II.

pZEN0042#b is shown in FIG. 3.

2. Cloning of T7 Expression Elements

2(i) T7 Terminator

The T7 terminator sequence from T7 gene 10 was cloned as annealed synthetic oligomers #5 and #6 (Table 1) between the Hind III and Bgl II sites of pZEN0042#b to generate pZEN0042#c (FIG. 4).

2(ii) tRNA$^{arg5}$

Figure 5:
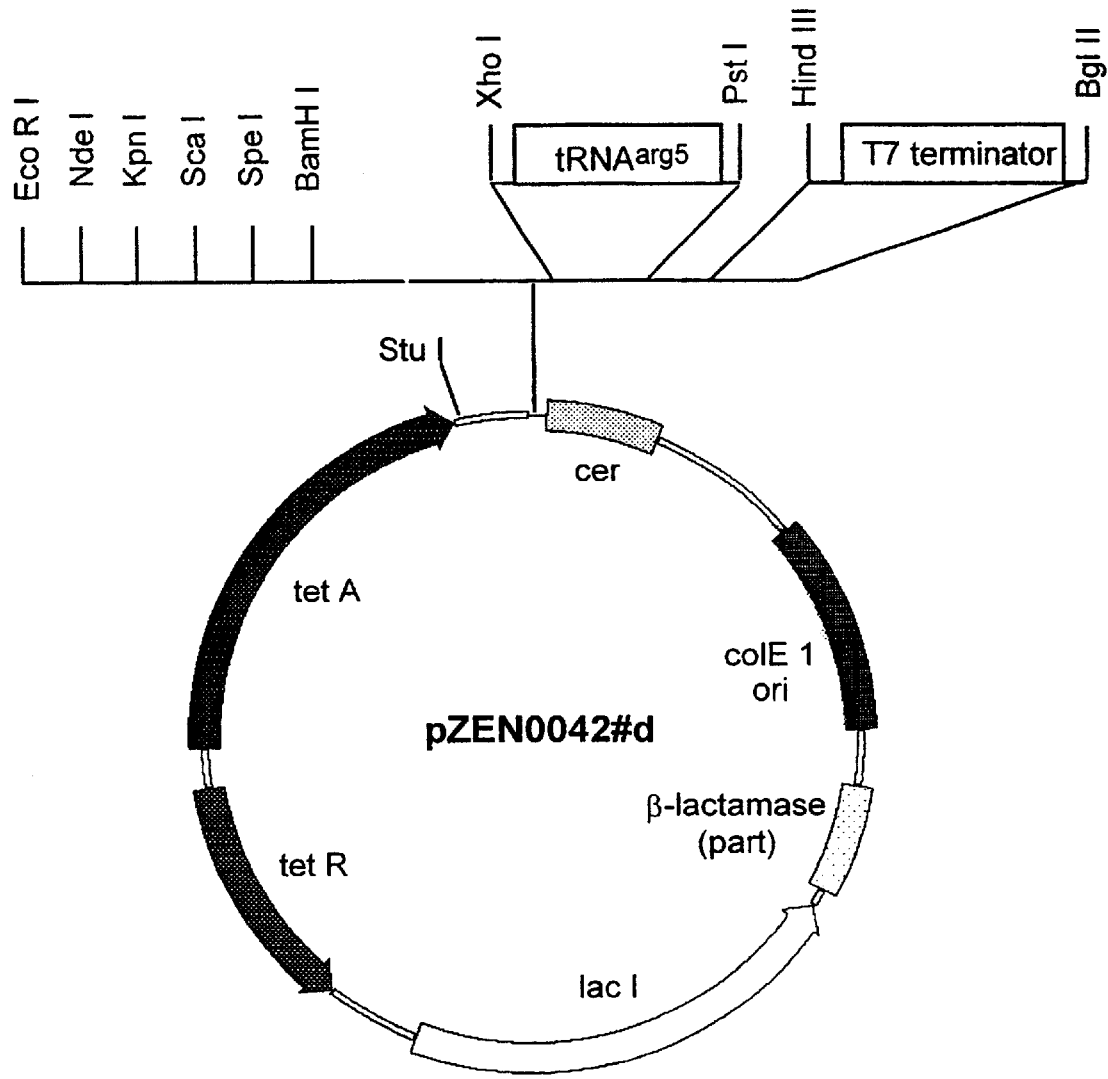
FIG. 5 shows the pZEN0042#d plasmid.

The tRNA$^{arg5}$ transcriptional reporter sequence (Lopez, P J et al, (1994), NAR 22, 1186–1193, and NAR 22, 2434) was cloned as annealed synthetic oligomers #7 and #8 (Table 1) between the Xho I and Pst I sites in pZEN0042#c to generate pZEN0042#d (FIG. 5).

2(iii) Upstream Terminator

Figure 6:
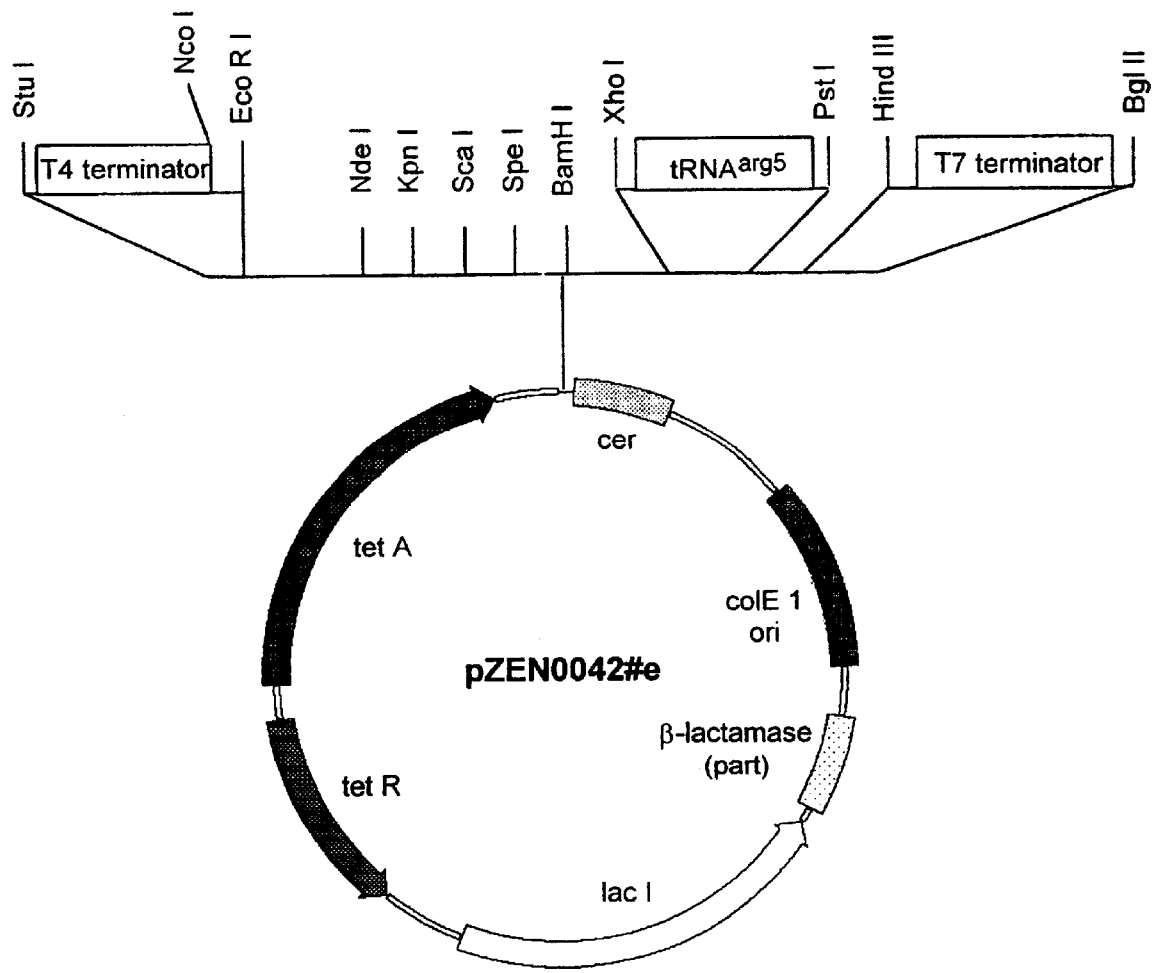
FIG. 6 shows the pZEN0042#e plasmid.

As the tetA sequence has no recognisable terminator a T4 terminator sequence was cloned upstream of the EcoR I site to reduce potential transcriptional readthrough from tetA (or any other unidentified promoter sequence) into the T7 expression cassette (to be cloned downstream of the EcoR I site). Annealed synthetic oligomers #9 and #10 (Table 1) containing the T4 terminator sequence and an additional Nco I site were cloned between the Stu I and EcoR I sites in pZEN00424#d to generate pZEN0042#e (FIG. 6).

2(iv) T7 Promoter with Perfect Palindrome Operator

Figure 7:
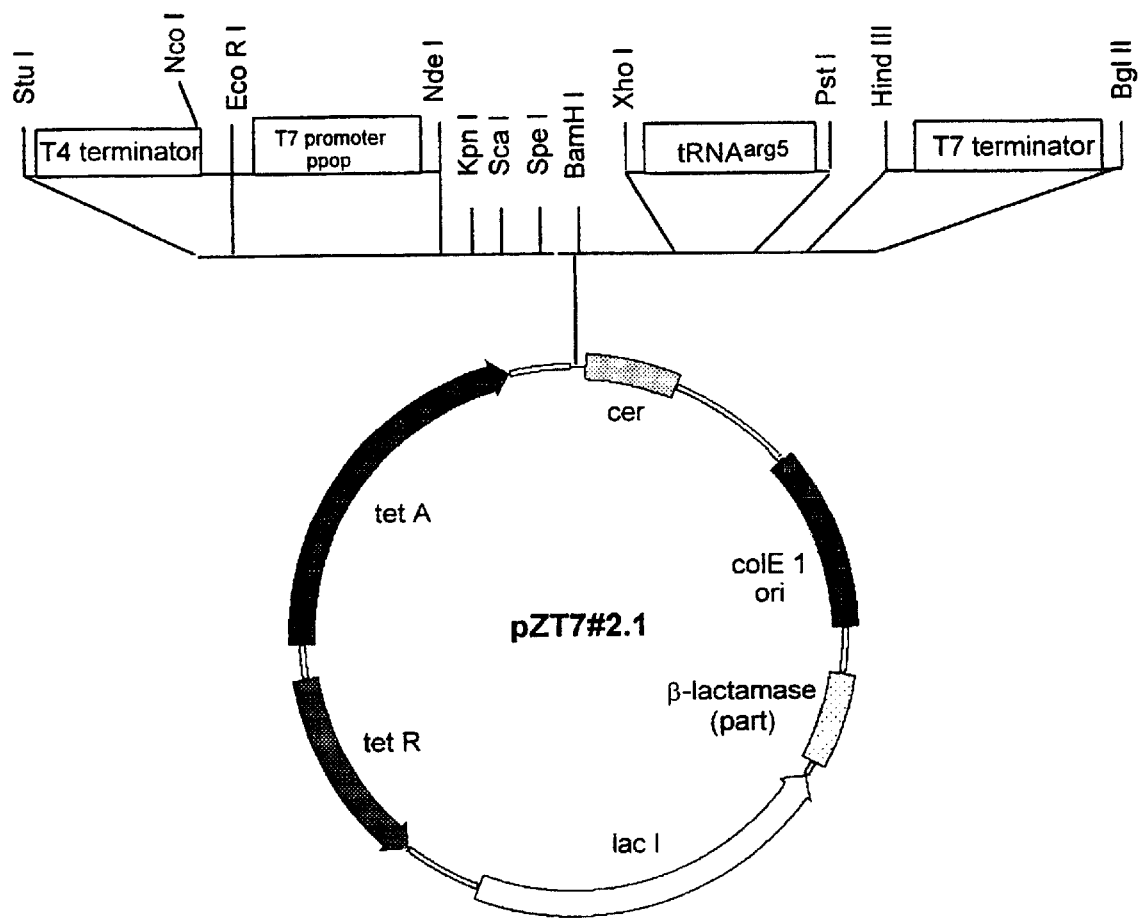
FIG. 7 shows the pZT7#2.1 plasmid.

The T7 gene 10 promoter incorporating a perfect palindrome lac operator sequence (Simons et al (1984), PNAS 81, 1624–1628) was cloned as annealed synthetic oligomers #11 and #12 (Table 1) between the EcoR I and Nde I sites of pZEN0042#e to generate pZT7#2.1 (FIG. 7).

2(v) Upstream Perfect Palindrome Lac Operator

Figure 8:
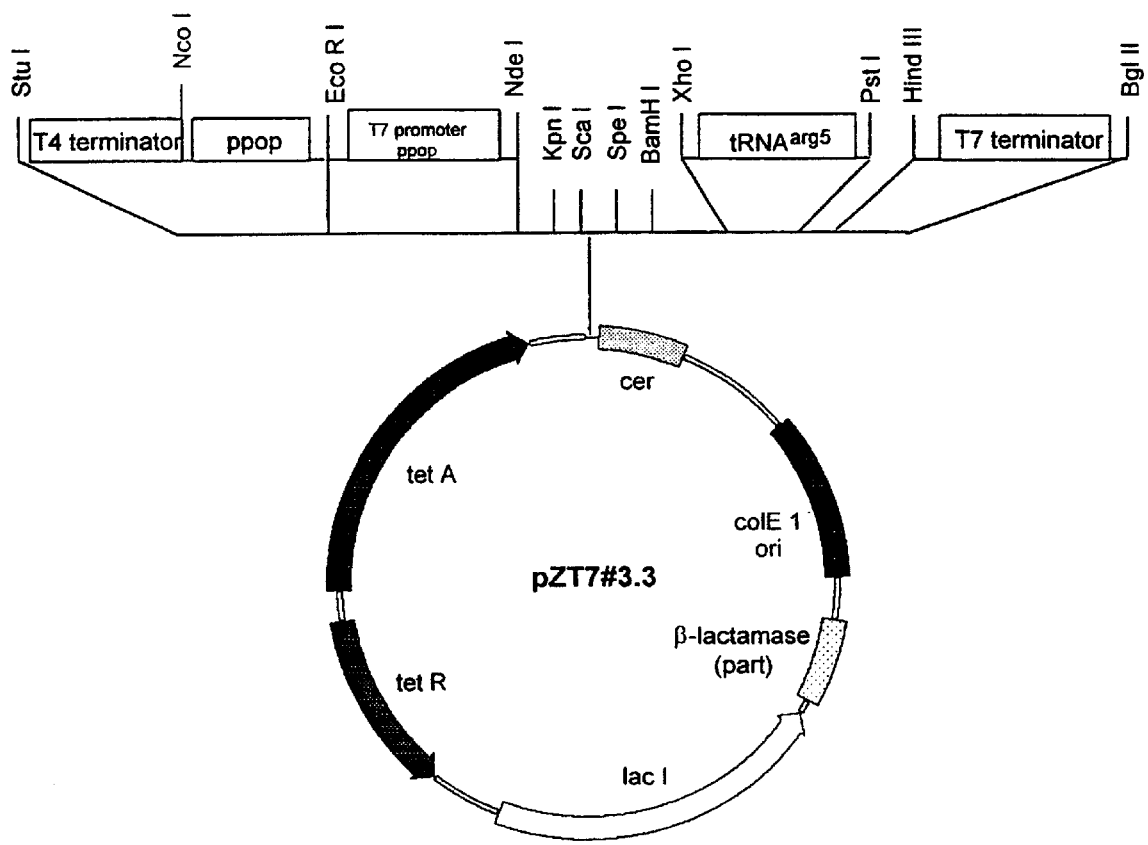
FIG. 8 shows the pZT7#3.3 plasmid.

A perfect palindrome operator sequence was positioned 94 bp upstream of the lac operator sequence of pZT7#2.1 by cloning of annealed synthetic oligomers #13 and #14 between the Nco I and EcoR I sites of pZT7#2.1 to generate pZT7#3.3 (FIG. 8).

---

What is claimed is:

1. A protein selected from [V9A]MCP1(9-76) (SEQ ID NO: 9), [V9G]MCP1(9-76) (SEQ ID NO: 26) or [V9T]MCP1(9-76) (SEQ ID NO: 29).

2. A protein according to claim 1 selected from [V9A]MCP1(9-76) (SEQ ID NO: 9) or [V9G]MCP1(9-76) (SEQ ID NO: 26).

3. A protein according to claim 1 which is [V9A]MCP1(9-76) (SEQ ID NO: 9).

4. [V9A]MCP1 (9-76) (SEQ ID NO: 9) protein according to claim 3 having Met-[V9A]MCP1 (9-76) (SEQ ID NO: 9) impurity present at a level of about 1% or less when analyzed by any one of reverse phase HPLC, capillary zone electrophoresis, Edman degradation or electrospray mass spectrometry.

5. A polynucleotide sequence encoding a protein selected from [V9A]MCP1 (9-76) (SEQ ID NO: 9), [V9G]MCP1(9-76) (SEQ ID NO: 26) or [V9T]MCP1(9-76) (SEQ ID NO: 29).

6. A polynucleotide sequence according to claim 5 encoding a protein selected from [V9A]MCP1(9-76) (SEQ ID NO: 9) or [V9G]MCP1(9-76) (SEQ ID NO: 26).

7. A polynucleotide sequence according to claim 5 encoding a protein which is [V9A]MCP1(9-76) (SEQ ID NO: 9).

8. A vector comprising a polynucleotide sequence as defined in claim 5.

9. A vector according to claim 8 which is an expression vector for intracellular expression in E. coli.

10. A vector according to claim 9 which is pZT7#3.3.

11. A host cell comprising a vector as defined in claim 8.

12. A method of making a protein selected from [V9A]MCP1 (9-76) (SEQ ID NO: 9), [V9G]MCP1 (9-76) (SEQ ID NO: 26) or [V9T]MCP1 (9-76) (SEQ ID NO: 29) which comprises culture of a host cell as defined in claim 11 in a culture medium under conditions for expression of the protein.

13. A method according to claim 12, further comprising at least partially purifying the protein.

14. A pharmaceutical composition comprising a protein as defined in claim 1, 2, 3 or 4 in association with a pharmaceutically-acceptable diluent or carrier.

* * * * *